(12) United States Patent
Brunel

(10) Patent No.: US 6,186,980 B1
(45) Date of Patent: Feb. 13, 2001

(54) SINGLE-USE DEVICE FOR INJECTION

(75) Inventor: Marc Brunel, Toulouse (FR)

(73) Assignee: Sanofi-Synthelabo, Paris (FR)

( * ) Notice: Under 35 U.S.C. 154(b), the term of this patent shall be extended for 0 days.

(21) Appl. No.: 09/499,645

(22) Filed: Feb. 8, 2000

(30) Foreign Application Priority Data

Oct. 7, 1999 (FR) .................................................. 99 12500

(51) Int. Cl.$^7$ ...................................................... A61M 5/32
(52) U.S. Cl. ........................... 604/110; 604/192; 604/198; 604/263
(58) Field of Search ..................... 604/110, 192, 604/198, 187, 263, 218, 220, 221, 222, 135, 136; 128/919

(56) References Cited

U.S. PATENT DOCUMENTS

| | | | |
|---|---|---|---|
| 5,709,662 | * | 1/1998 | Olive et al. ........................ 604/110 X |
| 5,713,871 | * | 2/1998 | Stock ................. 604/198 X |
| 5,749,856 | * | 5/1998 | Zadini et al. ...................... 604/198 X |
| 5,795,336 | * | 8/1998 | Romano et al. ...................... 604/192 |
| 5,893,845 | * | 4/1999 | Newby et al. ......................... 604/198 |
| 5,947,936 | * | 9/1999 | Bonds .................... 604/263 |

FOREIGN PATENT DOCUMENTS

| | | |
|---|---|---|
| 0 307 367 | 3/1989 | (EP) . |
| 0 446 551 | 9/1991 | (EP) . |
| WO 91/13634 | 9/1991 | (WO) . |
| WO 92/18187 | 10/1992 | (WO) . |
| WO 93/23089 | 11/1993 | (WO) . |
| WO 93/25254 | 12/1993 | (WO) . |
| WO 98/48869 | 11/1998 | (WO) . |
| WO 99/47194 | 9/1999 | (WO) . |

* cited by examiner

*Primary Examiner*—John D. Yasko
(74) *Attorney, Agent, or Firm*—Young & Thompson

(57) ABSTRACT

The invention relates to a single-use device for injection, which comprises a conventional syringe (1) and a device for protection of the injection needle (2) of this syringe (1) after use, comprising a protective sheath (7) which consists of two, rear (9) and front (8) bodies, which are designed to be rendered integral, one in the extension of the other, and a ring (24) which is accommodated in the rear body (9) and is provided with means (29, 31) for locking the syringe (1), the said ring being designed to be displaced between a first position, for injection, and a second position, for protection after use of the injection needle (2), by means of a spring (42) which is kept compressed in the position for injection, and is released when injection is completed.

13 Claims, 10 Drawing Sheets

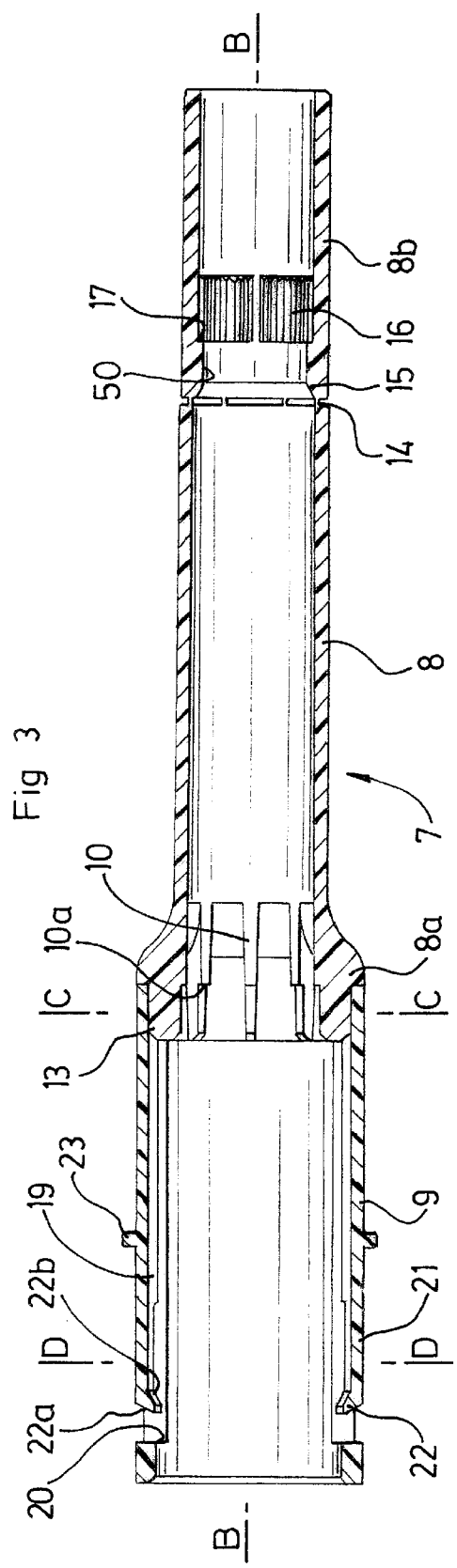
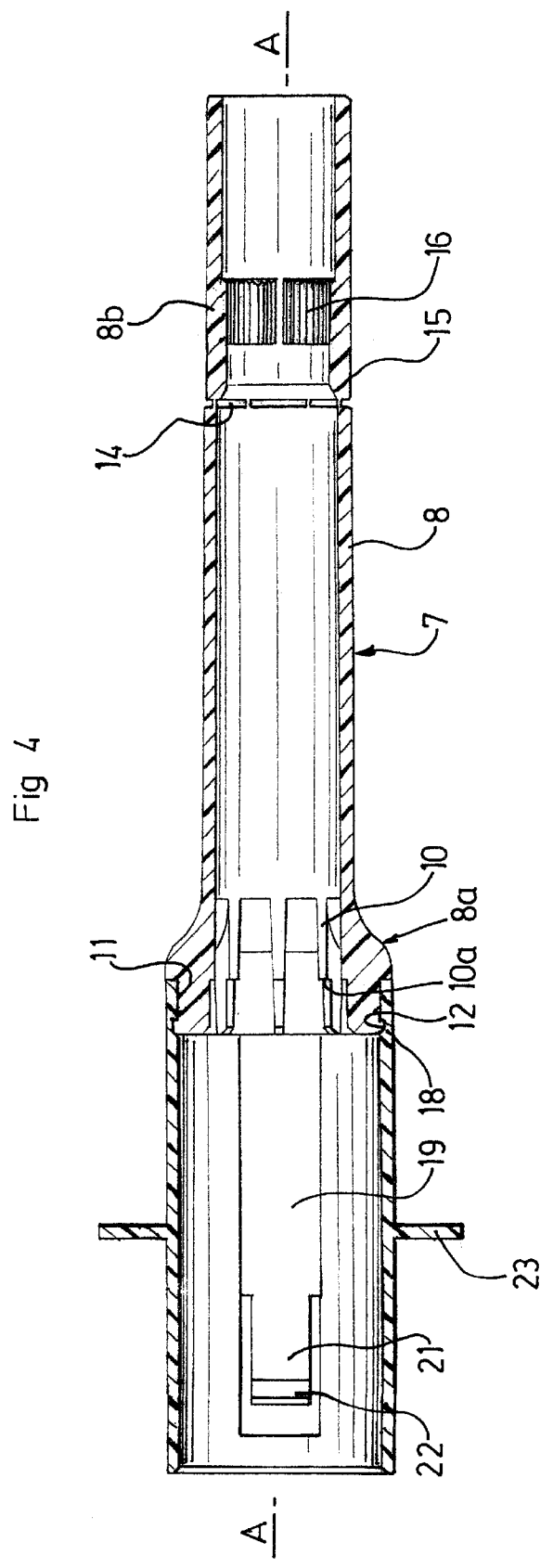

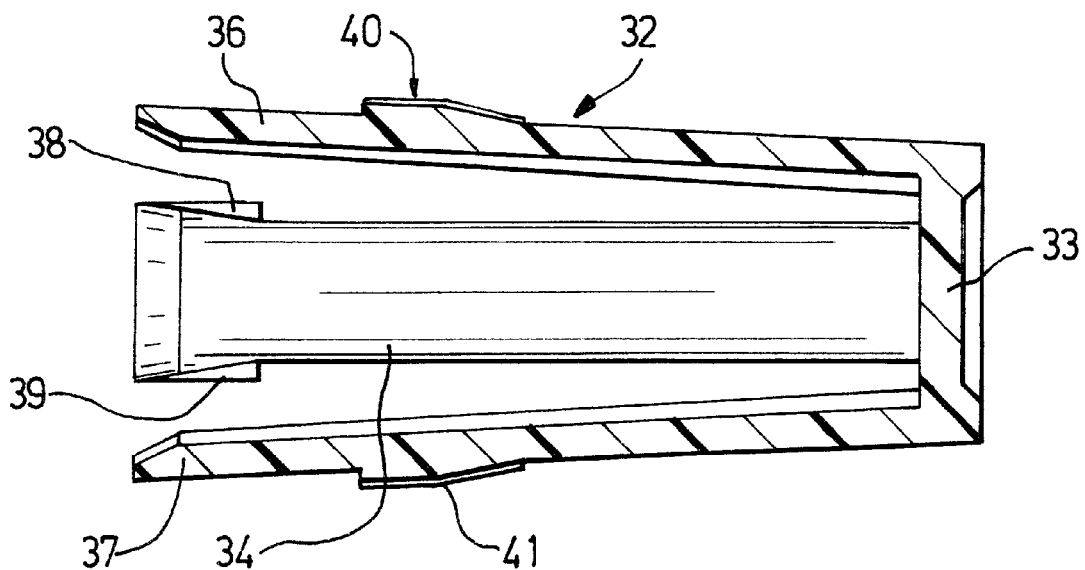
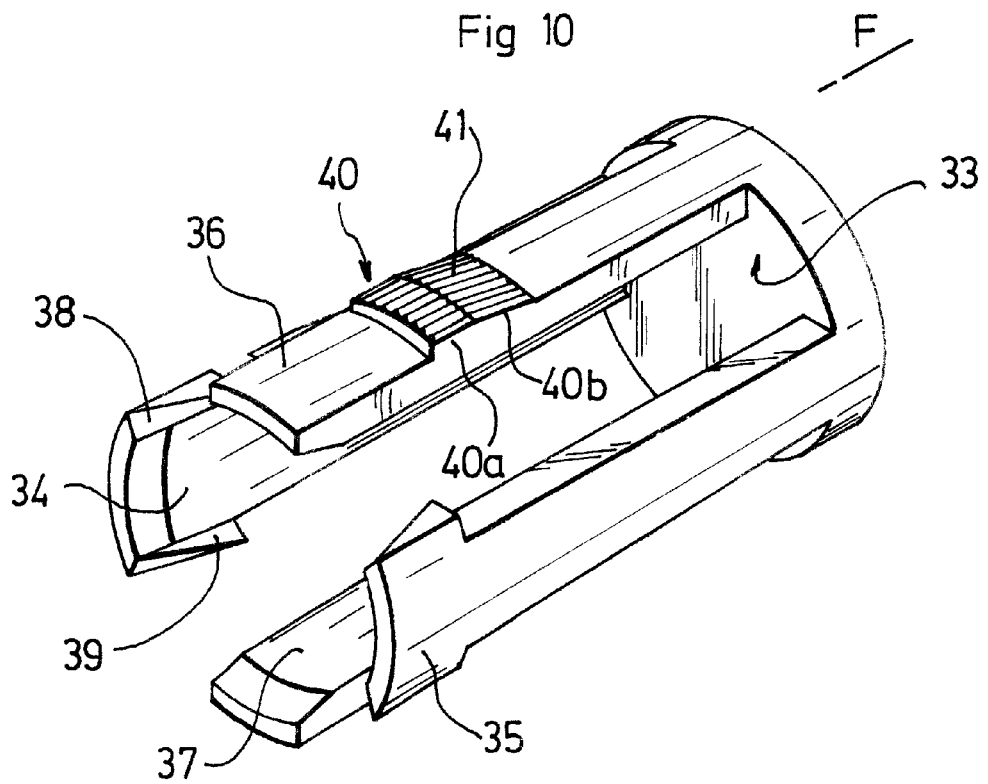

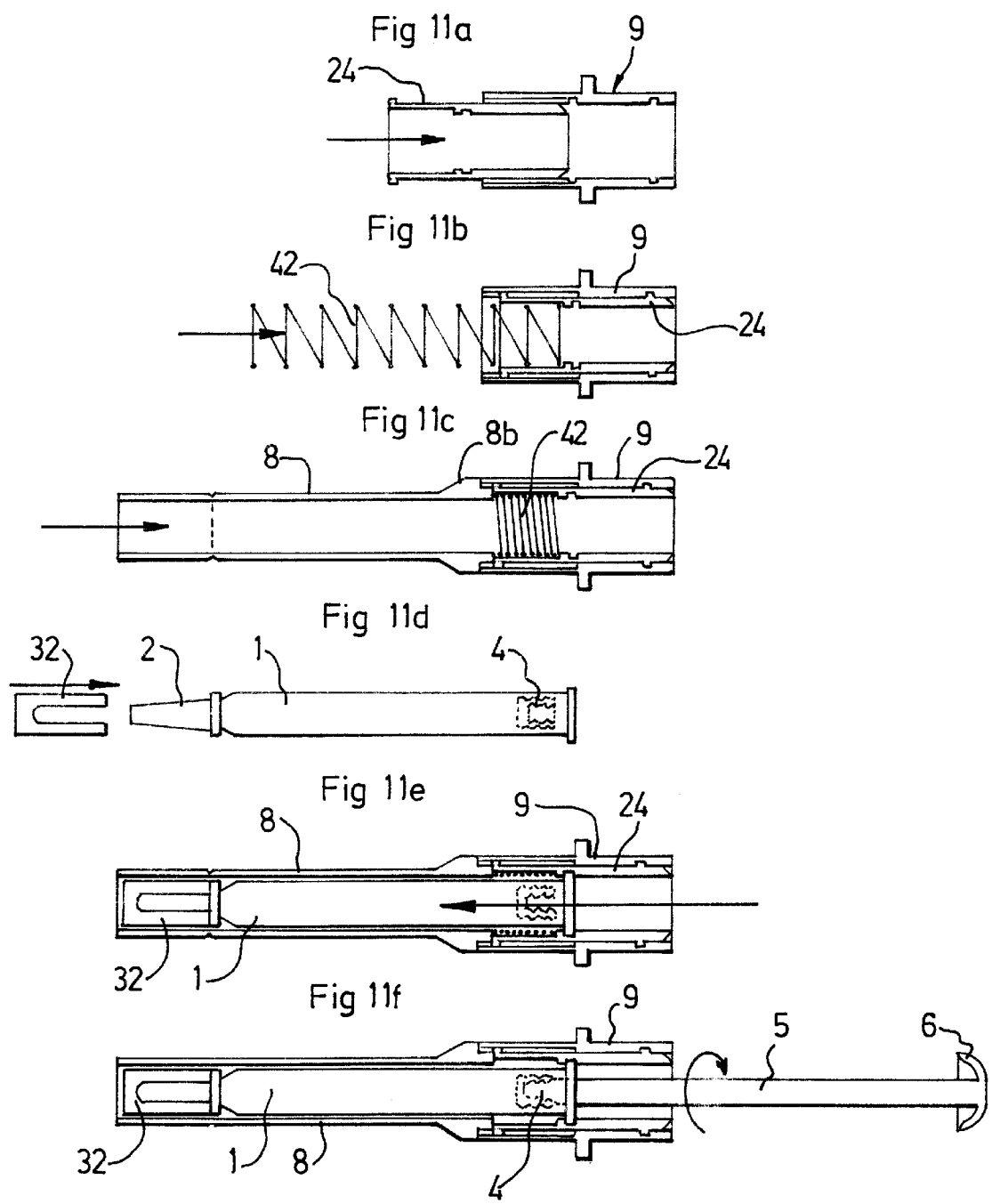

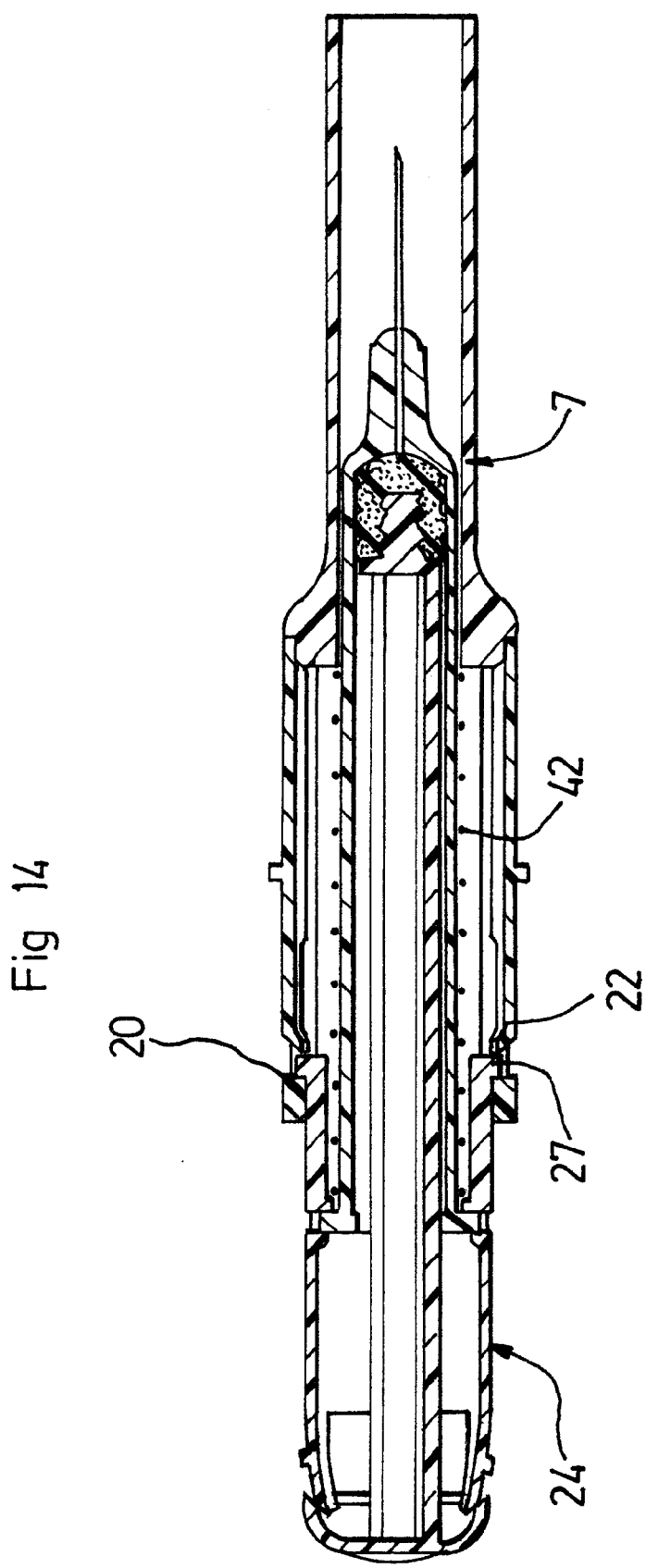

SINGLE-USE DEVICE FOR INJECTION

The invention relates to a single-use device for injection, which is designed to be pre-filled with a dose of fluid to be injected.

The single-use devices for injection which are conventionally used at present consist of pre-filled syringes, which are provided with a cap which is designed to protect the needle before use, then is removed so that the injection can take place, and is finally put back into position after the injection has taken place, in order to prevent further risks of being pricked by the contaminated needle.

However, it has been found that a design of this type has a major disadvantage, which is derived from the fact that when the needle is capped once more, the cap must be presented opposite the end of this needle. This requirement has in fact been found to be the cause of accidents, consisting of pricking which occurs relatively frequently, with all the risks involved in being pricked in this manner by a contaminated needle. Furthermore, syringes of this type do not have any safety device which is designed to prevent them from being re-used, and particular care must therefore be taken to destroy them.

In order to eliminate these disadvantages, the conventional technique consists of providing the device for injection with a protective sheath which can slide along the body of the syringe, or inside which the syringe can be retracted, such as to obtain either a position for injection, in which the injection needle is released, or a position for protection after use, in which this injection needle is accommodated and protected inside the protective sheath.

According to this principle, a conventional solution consists of providing devices for injection which have resilient means interposed between the syringe body and the protective sheath, which are designed to be kept compressed, and to assure positioning of the protective sheath and the syringe in their position for injection, before and during injection, and to relax and give rise automatically to sliding of the said protective sheath or the said syringe towards their position for protection after use, when injection is completed.

This solution makes it possible to produce devices for injection as described in the international patent applications WO-91.13634, WO-93.23089, WO-93.25254, and European patent applications EP-446.551 and EP-307.367, which firstly prevent any risk of being pricked accidentally before and after the injection takes place, in particular since the protective sheath or the syringe are made to slide automatically by means of release of the resilient means, after the injection has taken place, and secondly prevent the syringe from being re-used.

However, these devices for injection require production of specific syringes, which therefore have a substantially higher cost than that of conventional syringes, such as the glass syringes which are produced at present in very large numbers at a very low cost.

In fact, no solution has been found to the problem which consists of obtaining a device for injection of this type, which is non-re-usable after injection, and is equipped with a conventional syringe.

The present devices of this type for injection also have another disadvantage, derived from the fact that when release takes place of the resilient means, which are controlled by unlocking means disposed in the piston rod, there is no guarantee that the syringe has been completely emptied, owing to the tolerances accepted concerning the length of the syringes when the latter are manufactured.

Since devices of this type for injection are designed to be used for the purpose of injection of very small quantities of fluids (of approximately one cubic millimeter), the quantity administered of which must be respected rigorously, this technical solution is unsuitable for fulfilling the requirements applicable.

The object of the present invention is to eliminate these disadvantages, and its substantial objective is to provide a device for injection which is easy to manufacture, which comprises a conventional syringe, and cannot be reused after injection has taken place.

A further objective of the invention is to provide a device for injection which guarantees injection of all of the dose of fluid.

For this purpose, the invention relates to a single-use device for injection, comprising a syringe which is provided with a front nose which supports an injection needle, and with a rear collar, the said syringe delimiting a chamber which is filled with a dose of fluid to be injected, and is sealed by a piston which is rendered integral with one of the ends of a piston rod, which is provided with a thruster at its opposite end.

According to the invention, this device for injection comprises a device for protection after the syringe has been used, comprising:

a protective sheath, consisting of two tubular bodies, which are known as the front body and the rear body, and are provided with assembly means which make it possible to render the bodies integral one in the extension of the other, the front body having a diameter which is conjugated relative to that of the syringe, and a length which is designed to accommodate the said syringe partially, and the rear body having a diameter which is larger than that of the collar of the said syringe, and comprising finger-support units;

a ring which is disposed in the rear body, which comprises means for locking the collar of the syringe, and can make it possible to introduce the said syringe, by presenting the needle opposite the rear body of the protective sheath;

the ring and the rear body comprising:

first means for relative locking in translation, which can make it possible to introduce the said ring in the said rear body, by presenting the ring opposite the surface of assembly of the latter with the front body, and defining a first locking position, known as the position for injection, which allows the injection to take place when the device for injection has been assembled;

second means for relative locking in translation, which define a second locking position, known as the position for protection after use, which is obtained after rearward sliding of the ring inside the rear body, in which the injection needle is accommodated in the front body;

the ring and the front body being provided with stop means, which can keep resilient means compressed in the first locking position, for injection; and the ring or the rear body comprising a rear portion which is deformable radially, and supporting the first locking means in translation, which portion is designed to be deformed by the thruster of the piston rod at the end of the path of the latter, such as to release the said first locking units, and to permit displacement of the ring towards its second locking position, for protection after use.

The device according to the invention, for protection of syringes, thus comprises four main elements (ring, front and rear body of the protective sheath, and resilient means), which are designed to be assembled such as to constitute a pre-assembled assembly in which a conventional syringe is then inserted, and which then provides protection of the needle after use, and prevents any re-use.

In addition, the device for protection is produced in a very simple manner, by means of steps which can easily be automated. In fact, this assembly is carried out in accordance with the following steps:

introduction of the ring into the rear body of the protective sheath, until it is positioned in the first locking position;

putting into place resilient means which are not compressed in the ring; and assembly of the rear and front bodies, leading to compression of the resilient means by the stop means of the said front body and of the ring.

This pre-assembled assembly makes it possible to put into place subsequently a conventional pre-filled syringe, which is locked when it is put into place in this manner, at its collar, in its position for injection, and then, after injection has taken place, it is brought into a position for protection, which prevents any re-use.

According to a preferred embodiment, the ring is made from a material which has a colour different from that of the protective sheath, such as, for reasons of safety in particular, to make it possible to identify a device for injection which has already been used.

In addition, advantageously, the front body of the protective sheath consists of a translucent material, in order to allow the syringe to be seen.

On the other hand, the rear body of the protective sheath is advantageously made from an opaque material, such as to conceal from view the release mechanism, which could disturb the practitioner and the patient.

In addition, and advantageously, the means for locking in translation of the ring and of the rear body of the protective sheath comprise:

at least one inner longitudinal groove which is provided in the rear body, and is extended by a rear locking cavity;

for each groove, two, rear and front locking catches, which are provided on the ring, and are designed to slide in the said groove, and to be accommodated in the locking cavity.

As well as defining the first and second positions for locking in translation, this arrangement gives rise to relative locking in translation of the ring and the rear body.

In addition, each locking cavity advantageously consists of an aperture which is provided in the peripheral wall of the rear body, and is delimited at the rear by an inner shoulder, and at the front by an inner catch in the form of an asymmetrical tooth, which is provided with an inclined front surface, and is supported by a deformable tab which is provided in the said peripheral wall of the rear body.

In addition, according to a preferred embodiment, the means for assembly of the front and rear bodies of the protective sheath comprise an inner annular groove, which is provided in the rear body, and an outer clip ring provided on the front body.

In addition, advantageously, for each groove in the rear body, the front body of the protective sheath comprises an outer lug, which can be accommodated in the said groove. This arrangement provides relative locking in rotation of the two bodies of the protective sheath.

The means for locking the collar of the syringe advantageously comprise at least one rear inner catch, which is provided in the ring, and consists of an asymmetrical tooth, which is provided with an inclined rear surface, and a front inner shoulder, which is provided in the ring, at a distance from each catch which is equivalent to the thickness of the said collar.

The stop means of the resilient means advantageously comprise the aforementioned shoulder which is provided in the ring, and an inner shoulder which is provided in the front body, at a rear portion of the latter, which has an inner diameter which is larger than its regular inner diameter.

In addition, advantageously, the deformable portions which support the first units for locking in translation consist of two tabs which can be deformed radially, and extend in the rear extension of the ring, and on each of which there is disposed a rear locking catch.

In addition, each rear locking catch is advantageously disposed in an intermediate position along the length of the tab, such that to the rear of the said catches, there is provided a ramp, which, when injection is completed, for as long as force is exerted on the thruster, makes it possible to absorb the variations of lengths of the syringes, and thus to guarantee injection of all of the dose of fluid.

In addition, advantageously, the thruster of the piston rod has the shape of a bowl which is provided with an edge with an oblique profile, and each tab has a rear section with an additional oblique profile.

Other characteristics, objects and advantages of the invention will become apparent from the following detailed description provided with reference to the attached drawings, which show by way of example a preferred, non-limiting embodiment. In these drawings:

FIG. 3 is a longitudinal cross-section through an axial plane A of this protective sheath;

FIG. 4 is a longitudinal cross-section through an axial plane B of this protective sheath;

FIG. 9 is a longitudinal cross-section through an axial plane F of the claw-type joining piece of this device for injection;

FIG. 10 is a perspective view of this claw-type joining piece;

FIGS. 11a to 11f are schematic views showing the successive production steps of this device for injection;

FIG. 14 is a longitudinal cross-section through an axial plane representing the device for injection in the position for protection after it has been used.

Figure 1:
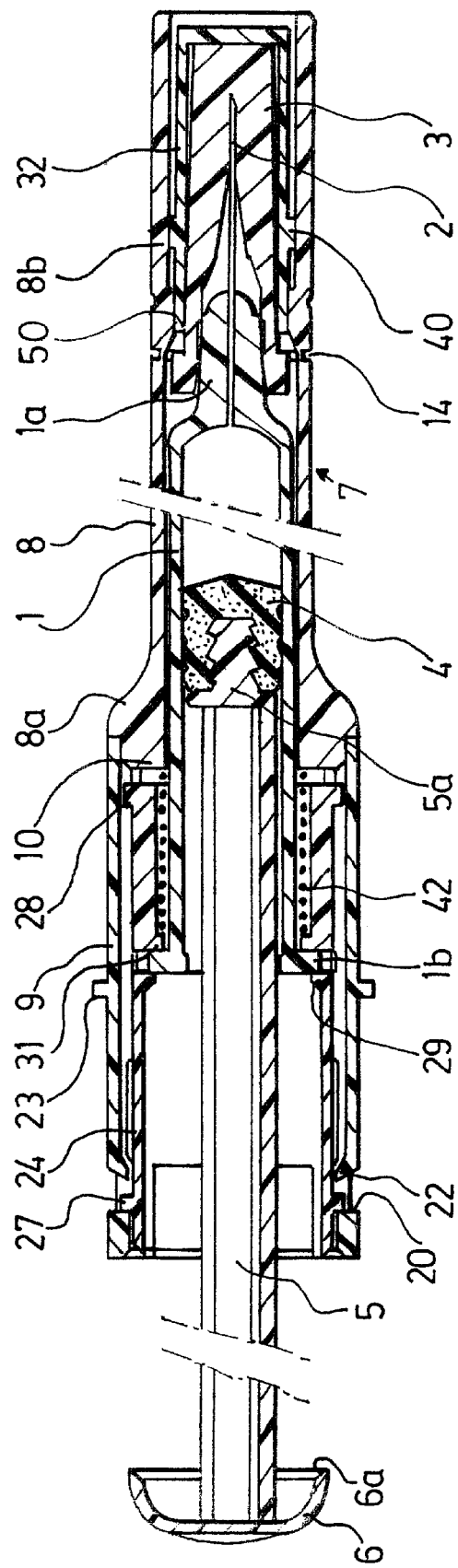
FIG. 1 is a longitudinal cross-section through an axial plane, of a device according to the invention for injection, shown before it is used.
Figure 2:
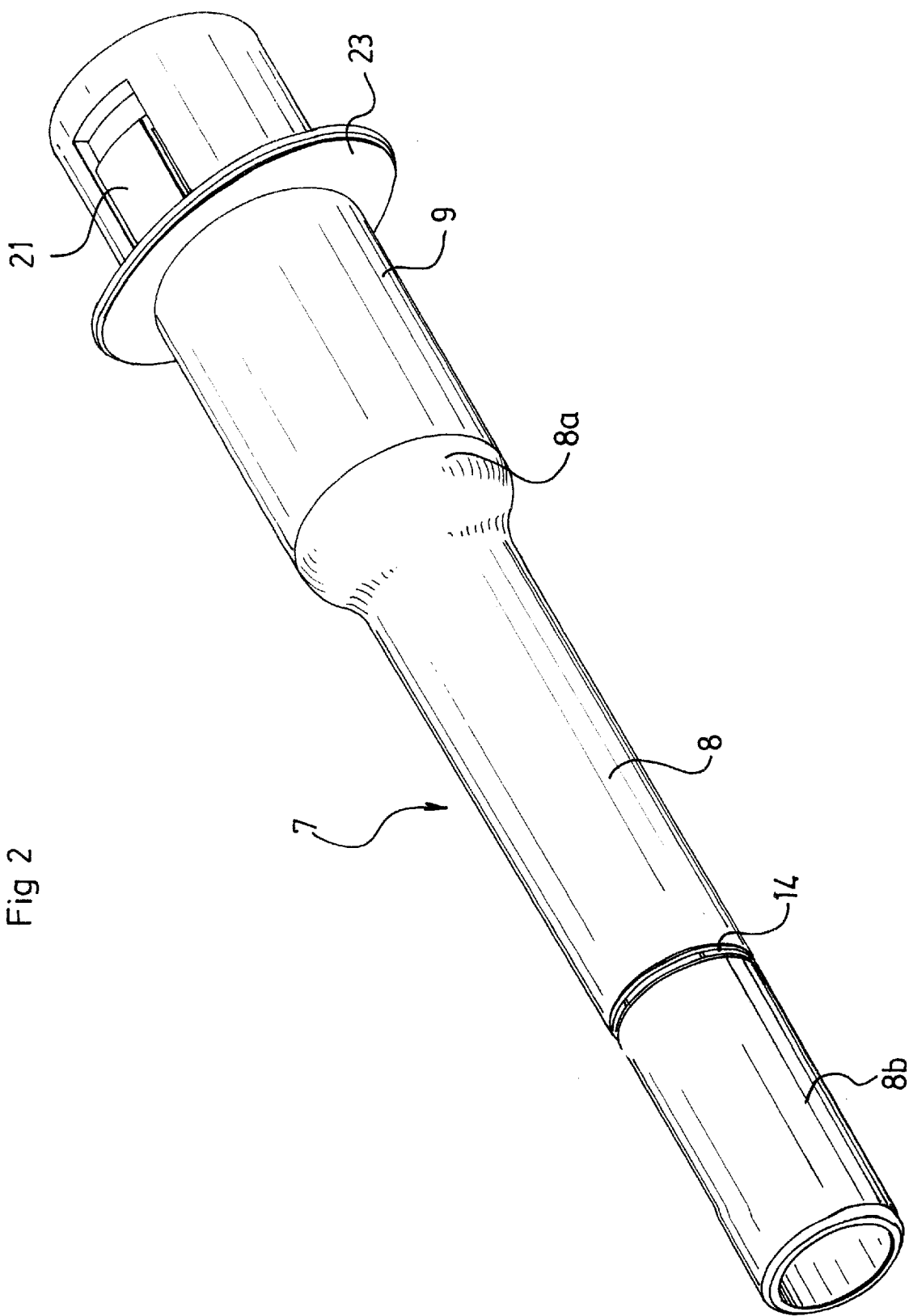
FIG. 2 is a perspective view of the protective sheath of this device for injection.

The device according to the invention for injection shown in FIG. 1 comprises firstly a pre-filled syringe 1 of the conventional type, which for example is made of glass, comprising in a conventional manner a front nose 1a, onto which there is fitted a needle 2, and a collar 1b at its rear end.

This syringe 1 also comprises in a conventional manner a cap 3 for protection of the needle 2, which is designed to be fitted in a sealed manner on the front nose 1a of the said syringe.

It also comprises in a conventional manner a piston 4, which delimits the chamber filled with a dose of fluid, which contains a blind threaded bore, into which there is screwed the threaded end 5a of a piston rod 5, which is provided at its opposite end with a thruster 6.

According to the invention, this thruster 6 is in the form of a bowl, which has a section 6a with an oblique profile, for the purposes explained hereinafter.

The injection device according to the invention also comprises an assembly for protection of the syringe 1, which is designed to be fully pre-assembled before the said syringe, which is initially pre-filled, is put into place in the said protective assembly.

This protective assembly comprises firstly a protective sheath 7, which is shown in FIGS. 2 to 6, consisting of two, front 8 and rear 9 tubular bodies, which are designed to be fitted one in the extension of the other.

The front body 8 has an inner diameter which is conjugated relative to the outer diameter of the syringe 1, and a length which is designed to accommodate the needle 2 provided with its protective cap 3, and is substantially 80% of the length of the syringe 1.

At its rear end, this front body 8 comprises a rear section 8a which has a substantially ovoidal outer shape, with outer diameters which are larger than the regular outer diameter of the said front body, and is hollow on the interior, such as to comprise inner longitudinal ribs such as 10, which define an inner diameter identical to that of the regular inner diameter of this front body 8.

Each of these ribs 10 additionally has a shoulder 10a, which delimits a rear end portion with an inner diameter which is substantially larger than the diameter of the syringe 1.

Figure 5:
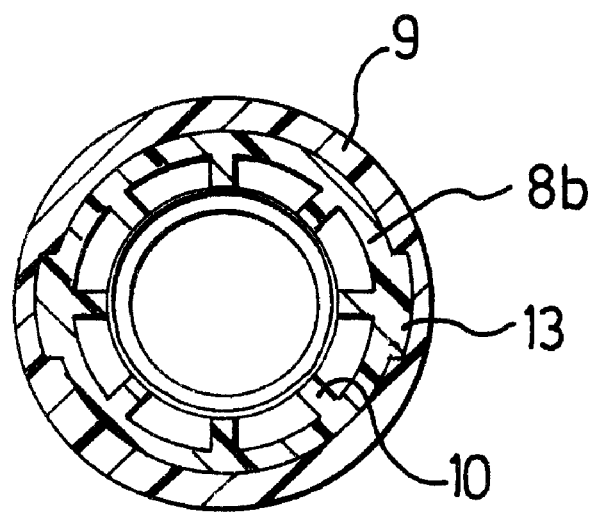
FIG. 5 is a transverse cross-section through a plane C of this protective sheath.
Figure 6:
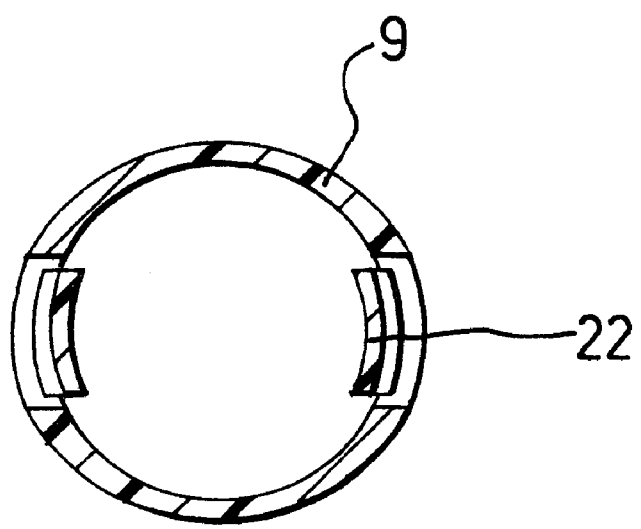
FIG. 6 is a transverse cross-section through a plane D of this protective sheath.

On the outer side, this rear section 8a comprises an annular groove 11 which is delimited by a rear clip ring 12. In addition, as shown in FIG. 5, this groove 11 is interrupted by two lugs such as 13, which are diametrically opposite, and project radially relative to the clip ring 12.

At its front end, the front body 8 comprises a front section 8b which can be separated, and is delimited by a breakable annular area 14, which is positioned such as to be disposed substantially at the front nose la of the syringe 1, when the latter has been put into place.

This section 8b which can be separated has on its interior, at its rear end, an oblique profile 15, which forms a ramp, delimiting a rear portion which constitutes a neck 50, with a diameter which is substantially smaller than that of the regular inner diameter of the front body 8.

At the front of this rear portion, the section 8b which can be separated additionally comprises a plurality of longitudinal catches such as 16, distributed on the periphery of the inner surface of the said section which can be separated, and delimiting an inner diameter which is identical to that of the said rear portion, such that the bases of the said catches define a shoulder 17 together with the front end of this rear portion.

Finally, with reference to this section 8b which can be separated, the front portion of the latter which is disposed at the front of the catches 16 has an inner diameter which is identical to the diameter which separates the base of the catches.

The rear body 9 has a substantially ovoidal shape, which is conjugated relative to that of the rear section 8a of the front body 8, and is designed to be fitted onto the said rear section 8a.

For this purpose, this rear body 9 firstly comprises an inner annular groove 18, which is designed to accommodate the clip ring 12. It also comprises two inner, diametrically opposite longitudinal grooves such as 19, which can each accommodate a lug 13, such as to ensure locking in rotation of the two bodies 8, 9, the said grooves being interrupted at a short distance from the rear end of this rear body 9, such that the latter has an inner shoulder 20 at the level of the end of these grooves 19.

Figure 7:
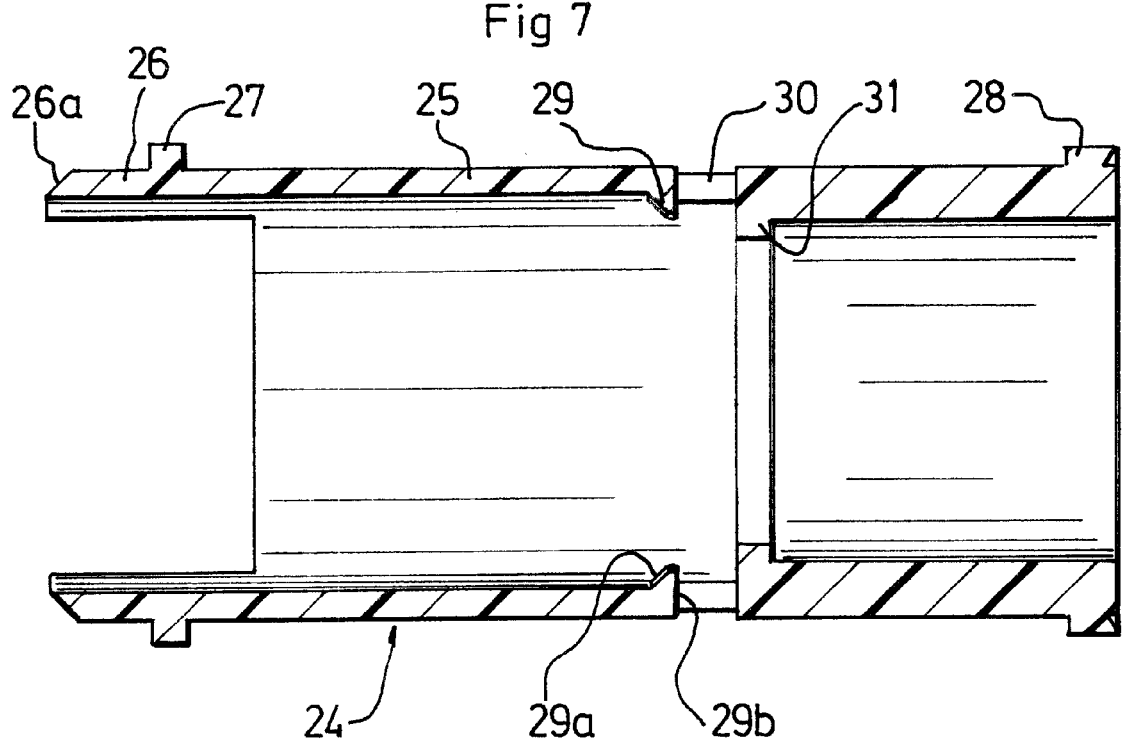
FIG. 7 is a longitudinal cross-section through an axial plane E of the locking ring of this device for injection.
Figure 8:
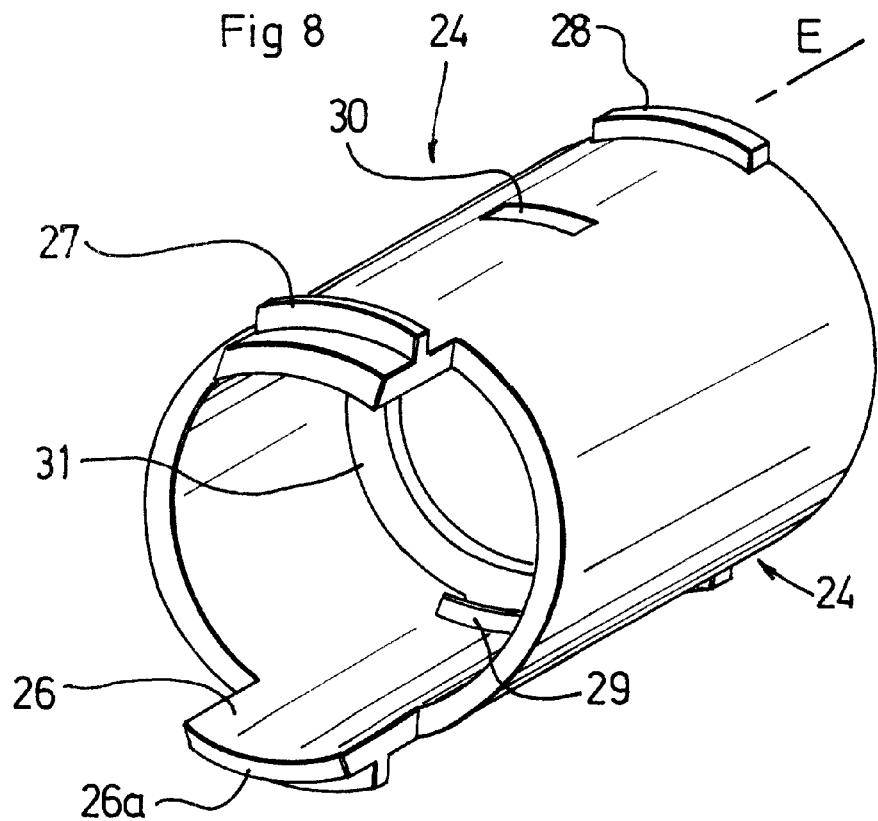
FIG. 8 is a perspective view of this locking ring.

As shown in FIG. 7, the grooves 19 are provided according to the larger diameter of the rear body 9, such as to minimise the thickness of the wall of the said rear body.

The rear body 9 additionally has two deformable tabs such as 21, each of which is provided in a groove 19 at the rear end of the latter, and each of which is formed from a cut-out in the shape of a U provided in the wall of the said rear body.

At its rear end, each of these tabs 21 comprises a transverse hook 22, which projects inside the rear body 9. Each of these hooks comprises a substantially radial anti-return rear surface 22a, and an oblique front surface 22b which forms a ramp.

Finally, the rear body 9 comprises a conventional finger-support outer collar 23.

Secondly, the protective assembly comprises a locking ring 24, which has a shape which is designed to be inserted in the rear body 9, when it is presented opposite the front surface of the latter.

This locking ring 24, which has a length which is designed to be inserted in the rear body 9, is in the form of a cylindrical sleeve 25, which is prolonged at the rear by two tabs such as 26, which are diametrically opposite one another in the form of a sector of a cylinder.

Each of these two tabs 26 has firstly a rear end surface 26a with an oblique profile, which is complementary relative to that of the section 6a of the thruster 6 of the piston rod 5.

Also, substantially half-way along its length, each of these tabs 26 comprises a transverse outer rib 27, which is designed to be able to slide in one of the grooves 10 of the rear body 9.

Centred on the same generatrices as the transverse ribs 27, the cylindrical sleeve 25 of this locking ring 24 comprises two transverse ribs such as 28, which are also designed to slide in the grooves 10 of the rear body 9, and are provided at the front end of the said sleeve.

Substantially half-way along its length, and axially aligned with the aforementioned ribs 27, 28, this cylindrical sleeve 25 also comprises two diametrically opposite inner ribs such as 29, downstream from each of which the peripheral wall of the said sleeve is provided with an aperture such as 30, which permits ejection of the undercut piece.

Each of these inner ribs 29 has a rear surface 29a with an oblique profile which forms a ramp, and an anti-return locking radial front surface 29b.

Finally, downstream from the apertures 30, and at a distance from the inner ribs 29 which is conjugated relative to the thickness of the collar 1b of the syringe 1, the cylindrical sleeve 25 comprises an annular inner shoulder 31.

Finally, the injection device according to the invention comprises a joining piece 32 with claws, which is shown in FIGS. 9 and 10, and is designed to cover the protective cap 3, and to give rise to withdrawal of the latter after breakage of the breakable area 14 of the front body 8 of the protective sheath 7.

This joining piece 32 with claws has a cylindrical front wall 33, with a diameter which is designed to penetrate in the section 8b which can be separated, at the periphery of which there extend substantially at right-angles four separate longitudinal tabs 34, 35, 36, 37, which are distributed regularly relative to the axis of the said wall:

two tabs 34, 35 which are diametrically opposite, and are each provided at their free end with two lateral claws such as 38, 39, which are designed to be able to penetrate in the protective cap 3; and two other diametrically opposite tabs 36, 37, each of which has in an intermediate position along its length an outer boss such as 40, with an outer surface provided with longitudinal catches such as 41, which are conjugated relative to the catches 16 of the section 8b which can be separated. In addition, each boss 40 has a cylindrical rear portion 40a, which is preceded by an inclined front portion 40b which forms a ramp.

It should also be noted that, as shown in FIG. 9, when bedding-in takes place, the tabs 34–37 are in a substantially "open" position, i.e. they are inclined towards the exterior relative to the axis of the front wall 33.

Production of the above-described device for injection, as well as the interconnection of the various units of the component elements, is explained hereinafter with reference to FIGS. 11a to 11f.

The first step consists of introducing the locking ring 24 into the rear body 9 of the protective sheath 7, by presenting the latter opposite the front surface of the said rear body, until the ribs 27 abut the shoulder 20 (FIG. 11a). It should be noted that this putting into place is permitted by the resilience of the tabs 21, and the shape of the front surface 22b of the ribs 22, which forms a ramp which allows the said ribs to be by-passed.

It should also be noted that when the locking ring 24 has been put into position, it is locked in rotation relative to the rear body 9, as a result of the positioning of the ribs 27 in the grooves 19.

The second step consists of introducing a spiral spring 42 partially inside the locking ring 24, by-presenting the latter opposite the front surface of the said ring, until one of its ends abuts the shoulder 31 (FIG. 11b).

The third step consists of fitting the front body 8 onto the rear body, by co-operation of the clip ring 12 with the groove 18 (FIG. 11c). During this operation, the spring 42 is automatically compressed between the shoulders 10a of the ribs 10 and the shoulder 31. In addition, the front body 8 and the rear body are locked in rotation relative to one another, as a result of positioning of the lugs 13 in the grooves 19.

On completion of these three operations which can easily be automated, a fully-assembled protective assembly is obtained, inside which there can then be introduced the pre-filled syringe 1, as previously described.

Prior to this introduction, as shown in FIG. 11d, the joining piece 32 with claws is positioned on the protective cap 3 of the syringe 1, which at this stage is without the piston rod 5. During this positioning, the tabs 34–37 of the joining piece 32 with claws are simply positioned around the protective cap 3, without any risk of pushing the latter in, and damaging the needle 2 and/or destroying the seal.

The syringe 1 which is provided with the joining piece 32 with claws is then introduced into the rear body 9 of the protective sheath 7, until the collar 1b is locked between the ribs 29 and the shoulder 31 (FIG. 11e). It should be noted that this introduction is made possible by the fact that the ribs 29 can be deformed, and owing to the ramp-type form of the rear surface 29a of these ribs 29, which allows the latter to be by-passed by the collar 1b.

In addition, during this introduction, the joining piece 32 with claws is clamped on the protective cap 3, when the bosses 40 of the latter pass the level of the ramp 15 of the section 8b which can be separated and the neck 50, which passage is also facilitated by the ramp-type form of the front portion 40b of the said bosses.

It should also be noted that, as shown in FIG. 1, during this clamping, the claws 38, 39 penetrate the protective cap 3 downstream from the glass cone which is conventionally provided on the front nose of conventional syringes 1, and is designed to guarantee sealing. Thus, any risk of pushing in the protective cap 3 and therefore damaging the needle 2 and/or destroying the seal is eliminated.

When this step has been carried out, it should be noted that the joining piece 32 with claws and the protective sheath 7 are locked in rotation relative to one another, as a result of the co-operation of the respective catches 16, 41 of the latter. In addition, firstly, the protective cap 3 is locked in rotation relative to the joining piece 32 with claws, owing to the penetration in the latter of the claws 38, 39, and secondly, this joining piece 32 with claws, the protective sheath 7 and the locking ring 24, are also locked in rotation relative to one another, as previously explained.

The final step shown in FIG. 11f consists of rendering the piston rod 5 integral with the piston 4 in a conventional manner. This then provides an injection device which is ready to use, use of which is described hereinafter with reference to FIGS. 12 to 14.

Figure 12:
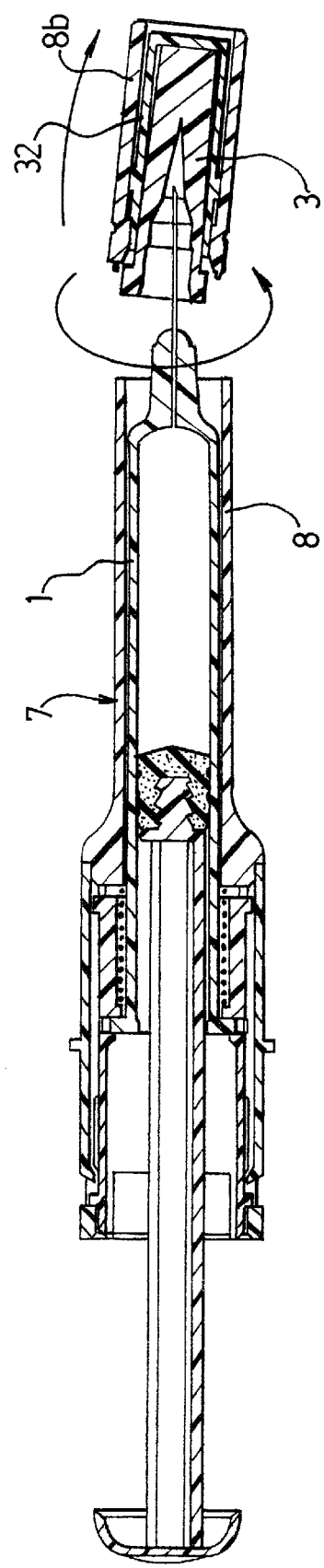
FIG. 12 is a longitudinal cross-section through an axial plane of this device for injection, showing the initial step of removal of the protective cap, for the purpose of use of the said device for injection.

Firstly, as shown in FIG. 12, the initial step consists of breaking the breakable area 14 in a conventional manner, by subjecting the section 8 which can be separated to rotary movement, and pulling this section. During the movement, since the assembled elements (protective cap 3, protective sheath 7, locking ring 24) are locked in rotation relative to one another, the protective cap 3 is firstly made to turn, thus facilitating detachment of the latter, then the joining piece 32 with claws is locked in translation relative to the section 8b which can be separated, by thrusting the bosses 40 against the shoulder 17, such that the protective cap 3 is removed simultaneously with the joining piece 32 with claws and with the said section which can be separated.

Figure 13:
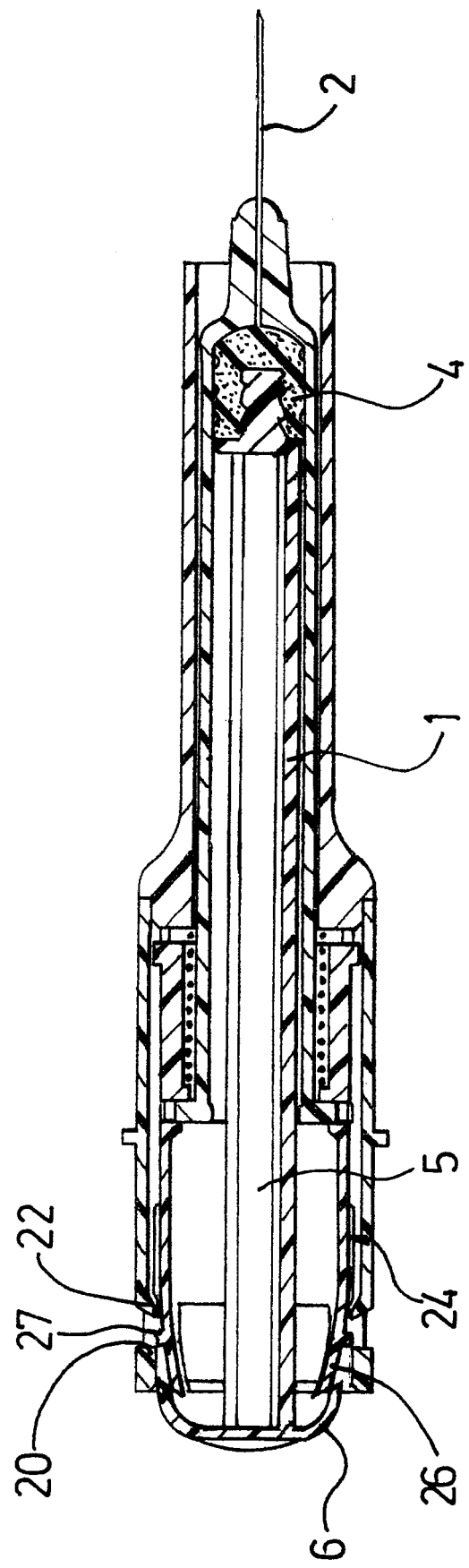
FIG. 13 is a longitudinal cross-section through an axial plane, representing the device for injection on completion of injection.

The injection can then be carried out in a conventional manner by means of antagonistic action on the thruster 6 and the finger-support collar 23. On completion of the injection, as shown in FIG. 13, the profiled edge 6a of the thruster 6 co-operates with the profiled edge 26a of the tabs 26 of the locking ring 24, causing the said tabs 26 to be deformed radially towards the interior, until the ribs 27 are released.

It should also be noted that since the ribs 27 are disposed in an intermediate position on the tabs 26, the latter have a ramp to the rear of the said ribs, which makes it possible to absorb the production tolerances of the syringes 1, and to ensure that the entire dose of fluid is delivered.

As shown in FIG. 14, when the injection has been completed, and force on the thruster 6 has ceased, the locking ring 24, which is thrust by the spring 42, is pushed back inside the protective sheath 7, and entrains the syringe 1, until the ribs 28 by-pass the ramp 22b of the ribs 22, and are locked between the said ribs 22 and the shoulder 20, thus preventing further use of the injection device.

Finally, and advantageously, the front body 8 of the protective sheath 7 is made of a translucent material, so that the syringe 1 can be seen. On the other hand, the rear body 9 of this protective sheath is made of an opaque material, so as to conceal the release mechanism from the sight of the user and the patient.

The locking ring 24 is made of a material which has a colour different from that of the rear body 9, such as to make it possible to identify immediately injection devices which have already been used.

What is claimed is:

1. Single-use device for injection comprising a syringe (1) which is provided with a front nose (1a) which supports an injection needle (2), and with a rear collar (1b), the said syringe delimiting a chamber which is filled with a dose of fluid to be injected, and is sealed by a piston (4) which is rendered integral with one of the ends of a piston rod (5), which is provided with a thruster (6) at its opposite end, the said device for injection being characterised in that it comprises a device for protection after the syringe (1) has been used, comprising:

a protective sheath (7), consisting of two tubular bodies (8, 9), which are known as the front body and the rear body, and are provided with assembly means (12, 18) which make it possible to render the bodies integral one in the extension of the other, the front body (8) having a diameter which is conjugated relative to that of the syringe (1), and a length which is designed to accommodate the said syringe partially, and the rear body (9) having a diameter which is larger than that of the collar (1b) of the said syringe, and comprising finger-support units (23);

a ring (24) which is disposed in the rear body (9), which comprises means (29, 31) for locking the collar (1b) of the syringe (1), and can make it possible to introduce the said syringe (2), by presenting the needle opposite the rear body (9) of the protective sheath (7);

the ring (24) and the rear body (9) comprising:
      first means (20, 22, 27) for relative locking in translation, which can make it possible to introduce the said ring in the said rear body, by presenting the ring opposite the surface of assembly of the latter with the front body (8), and defining a first locking position, known as the position for injection, which allows the injection to take place when the device for injection has been assembled;
      second means (20, 22, 28) for relative locking in translation, which define a second locking position, known as the position for protection after use, which is obtained after rearward sliding of the ring (24) inside the rear body (9), in which the injection needle (2) is accommodated in the front body (8);

the ring (24) and the front body (8) being provided with stop means (10a, 31), which can keep resilient means (42) compressed in the first locking position, for injection; and the ring (24) or the rear body (9) comprising a rear portion (26) which is deformable radially, and supporting the first locking means (27) in translation, which portion is designed to be deformed by the thruster (6) of the piston rod (5) at the end of the path of the latter, such as to release the said first locking units, and to permit displacement of the ring (24) towards its second locking position, for protection after use.

2. Device for injection according to claim 1, characterised in that the ring (24) is made of a material which has a colour different from that of the protective sheath (7).

3. Device for injection according to claim 1, characterised in that the front body (8) of the protective sheath (7) is made of a translucent material.

4. Device for injection according to any one of claim 1, characterised in that the rear body (9) of the protective sheath (7) is made of an opaque material.

5. Device for injection according to claim 1, characterised in that the means for assembly of the front body (8) and rear body (9) of the protective sheath (7) comprise an inner annular groove (18) which is provided in the rear body (9), and an outer clip ring (12) which is provided on the front body (8).

6. Device for injection according to claim 1, characterised in that the means for locking in translation of the ring (24) and of the rear body (9) of the protective sheath (7) comprise:

at least one inner longitudinal groove (19) which is provided in the rear body (9), and is extended by a rear locking cavity (20, 22);

for each groove (19), two, rear (27) and front (28) locking catches, which are provided on the ring (24), and are designed to slide in the said groove, and to be accommodated in the locking cavity.

7. Device for injection according to claim 6, characterised in that each locking cavity consists of an aperture which is provided in the peripheral wall of the rear body (9), and is delimited at the rear by an inner shoulder (20), and at the front by an inner catch (22) in the form of an asymmetrical tooth, which is provided with an inclined front surface (22b), and is supported by a deformable tab (21) which is provided in the said peripheral wall of the rear body (9).

8. Device for injection according to claim 6, characterised in that for each groove (19) in the rear body (9), the front body (8) of the protective sheath (7) comprises an outer lug (13), which can be accommodated in the said groove.

9. Device for injection according to claim 1, characterised in that the means for locking the collar (1b) of the syringe (1) comprise at least one rear inner catch (29), which is provided in the ring (24), and consists of an asymmetrical tooth, which is provided with an inclined rear surface (29a), and a front inner shoulder (31), which is provided in the ring (24), at a distance from each catch (29) which is equivalent to the thickness of the said collar.

10. Device for injection according to claim 9, characterised in that the stop means of the resilient means (42) comprise the shoulder (31) which is provided in the ring (24), and an inner shoulder (10a) which is provided in the front body (8), at a rear portion (8a) of the latter, which has an inner diameter which is larger than its regular inner diameter.

11. Device for injection according to claim 6, characterised in that the deformable portions which support the first units (27) for locking in translation consist of two tabs (26) which can be deformed radially, and extend in the rear extension of the ring (24), and on each of which there is disposed a rear locking catch (27).

12. Device for injection according to claim 11, characterised in that each rear locking catch (27) is disposed in an intermediate position along the length of the tab (26).

13. Device for injection according to claim 11, characterised in that the thruster (6) of the piston rod (5) has the shape of a bowl which is provided with an edge (6a) with an oblique profile, and each tab (26) has a rear section (26a) with a complementary oblique profile.

* * * * *